US012566201B2

(12) United States Patent
Vidarte Gordillo et al.

(10) Patent No.: US 12,566,201 B2
(45) Date of Patent: Mar. 3, 2026

(54) DETECTION MODULE, INTERFACE SYSTEMS AND METHOD FOR DETECTING INTERACTIONS OF A USER WITH A LIVING PLANT AND COMMUNICATING CONTROL SIGNALS

(71) Applicant: ARKYNE TECHNOLOGIES S.L., Viladecans (ES)

(72) Inventors: Pablo Manuel Vidarte Gordillo, Viladecans (ES); John Arturo Morales Matos, Viladecans (ES); Naroa Uria Moltó, Viladecans (ES)

(73) Assignee: ARKYNE TECHNOLOGIES S.L., Viladecans (ES)

( * ) Notice: Subject to any disclaimer, the term of this patent is extended or adjusted under 35 U.S.C. 154(b) by 1153 days.

(21) Appl. No.: 17/395,877

(22) Filed: Aug. 6, 2021

(65) Prior Publication Data

US 2022/0043043 A1     Feb. 10, 2022

(30) Foreign Application Priority Data

Aug. 7, 2020     (EP) .................................... 20382740

(51) Int. Cl.
| | |
|---|---|
| *G01R 27/26* | (2006.01) |
| *G01N 33/00* | (2006.01) |
| *G06F 3/01* | (2006.01) |

(52) U.S. Cl.
CPC .......... *G01R 27/2605* (2013.01); *G06F 3/011* (2013.01); *G01N 33/0098* (2013.01)

(58) Field of Classification Search
CPC ........ G01R 27/00; G01R 27/02; G01R 27/26; G01R 27/2605; G06F 3/00; G06F 3/01;
(Continued)

(56) References Cited

U.S. PATENT DOCUMENTS

| | | | | |
|---|---|---|---|---|
| 5,341,673 | A * | 8/1994 | Burns ................ | G01N 33/0098 |
| | | | | 73/73 |
| 9,341,659 | B2 | 5/2016 | Poupyrev et al. | |
| 2013/0221996 | A1 | 8/2013 | Poupyrev et al. | |

FOREIGN PATENT DOCUMENTS

| | | | | |
|---|---|---|---|---|
| CN | 203773942 | 8/2014 | | |
| CN | 109418144 | A * | 3/2019 | ........... A01C 23/047 |

(Continued)

OTHER PUBLICATIONS

European Search Report issued in EP 20382740, dated Feb. 1, 2021.

*Primary Examiner* — Hoai-An D. Nguyen
(74) *Attorney, Agent, or Firm* — ICE MILLER LLP

(57)     ABSTRACT

It is presented a detection module (10) for detecting capacitance variations in a plant (20), comprising one or more electrodes (11) configured and arranged to be put in electrical communication with the plant (20), one or more capacitive sensors (12) in electrical communication with the electrodes (11), configured to measure capacitance through the electrodes (11) and convert it to voltage values, a control unit (13) in communication with each capacitive sensor (12), having at least one electrical or wireless communication port (14', 14") to other detection modules (10) or to external devices (0), and being configured to read said voltage values, process them for obtaining processed voltage values, compare said processed voltage values with a threshold value, and send a control signal to one or more external devices (0) via said at least one communication port (14', 14") when said processed voltage values exceed the threshold value, and a user-accessible potentiometer (15) in electrical communication with the control unit (13), the potentiometer (15) being configured to adjust said threshold value. It is also presented an interface system and a method for detecting interactions of a user with a living plant and
(Continued)

1 communicating control signals using at least one of said detection module (10).

6 Claims, 5 Drawing Sheets

(58) Field of Classification Search
CPC ........ G06F 3/011; G01N 33/00; G01N 27/00;
G01N 27/02; G01N 27/22; G01N
33/0098; G01N 27/228; G11B 19/00;
G11B 19/02; G11B 19/06; H03K 17/00;
H03K 17/94; H03K 17/96; H03K
2217/00; H03K 2217/94; H03K
2217/9401; H03K 2217/94026; H03K
2217/96; H03K 2217/9607; H03K
17/962; H03K 2217/960705; G01D 5/00;
G01D 5/12; G01D 5/14; G01D 5/24;
G01D 5/2405
USPC ................ 324/600, 649, 658, 663, 664, 665
See application file for complete search history.

(56) References Cited

FOREIGN PATENT DOCUMENTS

| | | | |
|---|---|---|---|
| DE | 102016202824 | 8/2017 | |
| EP | 0954206 | 11/1999 | |
| FR | 2850808 | 8/2004 | |
| JP | 2004061251 A * | 2/2004 | ............ G01N 27/22 |
| JP | 3833237 B1 * | 10/2006 | ............... A01G 7/04 |
| KR | 20180109806 A * | 10/2018 | ......... G01R 27/2605 |
| WO | 88/07291 | 9/1988 | |

* cited by examiner

DETECTION MODULE, INTERFACE SYSTEMS AND METHOD FOR DETECTING INTERACTIONS OF A USER WITH A LIVING PLANT AND COMMUNICATING CONTROL SIGNALS

CROSS-REFERENCE TO PRIOR APPLICATION

This application claims priority to and the benefit thereof from European Patent Application No. EP20382740.7, filed Aug. 7, 2020, titled "DETECTION MODULE, INTERFACE SYSTEMS AND METHOD FOR DETECTING INTERACTIONS OF A USER WITH A LIVING PLANT AND COMMUNICATING CONTROL SIGNALS," the entirety of which is hereby incorporated herein by reference.

DESCRIPTION

The present invention relates to interactive systems using living plants. A first aspect relates to a detection module to detect user's interactions with a plant. A second and a third aspects of the present invention relates to two different interface systems for communicating control signals to one or more electronic devices. Finally, a fourth aspect of the present invention relates to a method for providing a user's interaction with living plants.

STATE OF THE ART

Interactive systems using living plants as interfaces to activate actions on devices are known in the state of the art. For example, document US2013221996A1 discloses a system with a detection module configured to measure changes in the impedance of a plant when a person approaches to it or touches it. After that, the system sends an order to a device to provide an action. Specifically, this system correlates the measured impedance curve with one or more predefined impedance curves, where each predefined impedance curve corresponds to a particular action performed by the user. Depending on the correlation obtained, the system orders one or another action.

In contrast, document CN203773942U discloses a system comprising a detection module that forms an RC oscillation circuit with a plant, which is isolated from the ground. A control chip sends signal pulses to the detection module and determines whether a person is touching the plant or not based on the charge time and the discharge time of the RC oscillation circuit.

However, living plants change shape and size, or the substrate they are planted on may vary in condition, making it difficult to keep detection modules in accurate calibration and make detections reliable over time.

Therefore, there is a need to provide a reliable system for providing accurate interpretations of user's interactions with a living plant.

DESCRIPTION OF THE INVENTION

The aim of the present invention is to provide a detection module, two different interface systems and a method for solving the previously cited necessity.

According to a first aspect of the present invention, it is provided a detection module for detecting capacitance variations in a plant, comprising:

one or more electrodes configured and arranged to be put in electrical communication with a plant, either by direct contact or through a moist substrate, one or more capacitive sensors in electrical communication with the electrodes, configured to measure capacitance through the electrodes and convert it to voltage values, and a control unit in electrical communication with each capacitive sensor, having at least one electrical or wireless communication port to other detection modules or to external devices, and being configured to read and process the voltage values obtained by the capacitive sensors, compare said processed voltage values with a threshold value provided to the control unit, and send a control signal to one or more external devices via the communication port when interprets that at least one processed voltage value has exceeded the threshold value.

The present detection module is characterized in that it comprises a user-accessible potentiometer in electrical communication with the control unit, the potentiometer being configured to adjust said threshold value. For example, the potentiometer's adjustment can be performed according to the natural capacitance established by the plant in its location. Thanks to this configuration, the detection module can be calibrated in an easy way when installed and permits feasibly detecting a capacitance change when a subject becomes electrically coupled to the plant—e.g., by touching it. Once the detection module has been calibrated using the potentiometer, the control unit may adjust any drift in the measured signal.

As it can be inferred, the detection module may comprise an input port for receiving a communication port from another detection module, and producing a series connection by several detection modules and the external devices.

In a preferred embodiment of said detection module, at least one of said electrodes and/or said potentiometer is arranged at the end of a shielded wire, in order to avoid electrical noise and other interferences from affecting the measured values.

In another preferred embodiment, the control unit is configured to apply a moving average algorithm to the voltage values provided by the capacitive sensors during a predetermined time interval, so an average voltage value is calculated. Said average voltage value is the one to be compared with the threshold value. When measured with an electrode, the natural capacitance from a plant is a quite instable value over time, which is turned into voltage oscillations and peaks by the capacitive sensor. Thanks to this configuration, the control unit obtains a more stable value to compare with the threshold value, and the plant-subject coupling detection becomes more reliable.

In another preferred embodiment, the control unit is further configured to measure a dwell time for which the processed voltage values rate above the threshold value and, if said dwell time is lower than a predetermined duration, avoid sending the corresponding control signal. In this embodiment, the control unit is able to measure the time the processed voltage values—averaged or not—are above the threshold value, and interpret that there has been a coupling between a subject and the plant when said time is longer than a predetermined minimum duration. In other words, the control unit is configured to send the corresponding order only when the trigger situation of a processed voltage value above the threshold value has a minimum duration. This minimum duration can be set between 100 milliseconds and 500 milliseconds, preferably 200 milliseconds. When the duration is less than said set time, the control unit is configured to discard the supposed coupling as a false positive. If the duration is longer than the set time, the control unit is configured to accept the coupling as true and activate the corresponding command.

During the coupling time, the voltage value may fluctuate and unintentionally fall below the threshold value. Therefore, in another preferred embodiment, the control unit is configured to, after been measured a dwell time higher than a predetermined dwell duration and been detected that the processed voltage values dropped below the threshold value, measure a holding time for which the processed voltage values rate below the threshold value and, if said holding time is lower than a predetermined holding duration, avoid sending a new corresponding control signal. In other words, the control unit is configured to measure the time in which said processed voltage values are below the threshold value after being accepted a coupling as true, in order to know if a drop is due to an involuntary oscillation or if it is due to the user having stopped being coupled to the plant and being coupled again. The minimum holding time for said fluctuation being accepted as a new coupling is between 100 milliseconds and 500 milliseconds, preferably 250 milliseconds.

For the previous purposes, the control unit may comprise one or more internal timers from where obtaining time intervals.

In another preferred embodiment, the capacitive sensors and the control unit are located in a housing, which comprises at least one opening through which the electrodes and the potentiometer access to the outside of the housing in an hermetic way. Thanks to this configuration, the detection module can be placed near the plant with no risk of short circuit when the plant is watered. Optionally, the housing is part of a pot, where a plant can be located.

In relation to the electrodes, at least one can be made of or comprise stainless metal, non-stainless metal and/or carbon. Regarding its shape, at least one electrode may include, but is not limited to, a bar-shaped geometry. In this case, the electrode has a length greater than 2 centimeters and a diameter greater than 2 millimeters.

According to a second aspect of the present invention, it is provided an interface system for communicating control signals to one or more electronic devices, comprising:
   one or more living plants, wherein the capacitance of any of them is changed when a subject becomes electrically coupled to it, and
   one or more detection modules as described in any of the above claims, This interface system is characterized in that one or more electrodes of each detection module is in electrical communication with each plant. Thanks to this configuration, it is provided a reliable system for accurately interpret the interactions of a subject with living plants.

In a preferred embodiment of said interface system, the living plants comprise roots buried in a moist substrate and at least one electrode is in direct contact with the moist substrate. It has been discovered that it is not necessary direct contact of the electrodes with plants for detecting a change in its capacitance—the electrodes being in electrical communication with the plant through a moist substrate is enough.

In another preferred embodiment, the interface system includes a hub, as well as more than one detection module in electrical or wireless communication with the hub. The hub is configured to receive said control signals from the detection modules and redirect them to corresponding external devices. Optionally, the hub may comprise a power port for powering the detection modules, which can be also a communication port. It may further comprise a power port for being powered, which can be also a communication port to an external device—such as a PC. Thanks to this hub, all the detection modules and plants can be interconnected and provide joint control actions.

In a preferred embodiment of the present interface system, at least one plant is of the crass kind. It has been discovered that the coupling interactions with crass kind plants are more feasible to measure, especially when measuring its capacitance.

According to a third aspect of the present invention, it is provided an interface system for communicating control signals to one or more electronic devices, comprising:
   one or more living plants, wherein an electric attribute of any of them is changed when a subject becomes electrically coupled to it, and
   one or more detection modules, each detection module comprising one or more sensors in electrical communication with at least one of said living plants and configured to measure said electric attribute of the plants and convert it to voltage values, and a control unit in electrical communication with the sensors and configured to read the voltage values and send a determined control signal to one or more external devices on the basis of the read voltage values, This interface system is characterized in that said living plants are of the crass kind. Thanks to this configuration, it is provided an interface system highly accurate when interpreting if a subject is interacting with it. It is advantageous measuring capacitance changes in a crass plant, but it is also possible detect coupling interactions of a user by means of any other electric attribute of the crass plant. This is due to the high water content of crass plants.

According to a fourth aspect of the present invention, it is afforded a method for providing a user's interaction with a living plant, comprising:
   measuring capacitance through one or more electrodes which are in electrical connection with the plant, wherein a change in the capacitance is caused by a subject becoming electrically coupled to the living plant,
   converting the measured capacitance into voltage values,
   comparing the voltage values with a threshold value, and
   sending a control signal to one or more external device when a voltage value exceeds the threshold value.

The present method is characterized in that further comprises adjusting said threshold value through a user-accessible potentiometer in electrical communication with the control unit before sending said control signal for the first time. For example, the potentiometer's adjustment can be performed according to the natural capacitance established by the plant in its location. Thanks to this configuration, the detection module can be calibrated in an easy way when installed and permits feasibly detecting a capacitance change when a subject becomes electrically coupled to the plant— e.g., by touching it. Once the detection module has been calibrated using the potentiometer, the control unit may adjust any drift in the measured signal.

In a preferred embodiment of the present method, it further comprises calculating average voltage values from said voltage values during a given time interval by applying a moving average algorithm, being said average voltage values the ones to be compared with the threshold value.

In another preferred embodiment, it further comprises measuring a dwell time for which the voltage values rate above the threshold value and, if said dwell time is lower than a predetermined dwell duration, avoiding sending the corresponding control signal. Optionally, it may further comprise, after been measured a dwell time higher than a predetermined dwell duration and been detected that the voltage values dropped below the threshold value, measuring a holding time for which the voltage values rate below the threshold value and, if said holding time is lower than a predetermined holding duration, avoid sending a new corresponding control signal.

BRIEF DESCRIPTION OF THE DRAWINGS

So that the manner in which the above recited aspects are attained and can be understood in detail, a more particular description of a preferred embodiment of the invention may be had by reference to the appended figures.

It is to be noted, however, that the appended figures illustrate only embodiments of this invention and is therefore not to be considered limiting of its scope, for the invention may admit to other equally effective embodiments.

DESCRIPTION OF PREFERRED EMBODIMENTS

Figure 1:
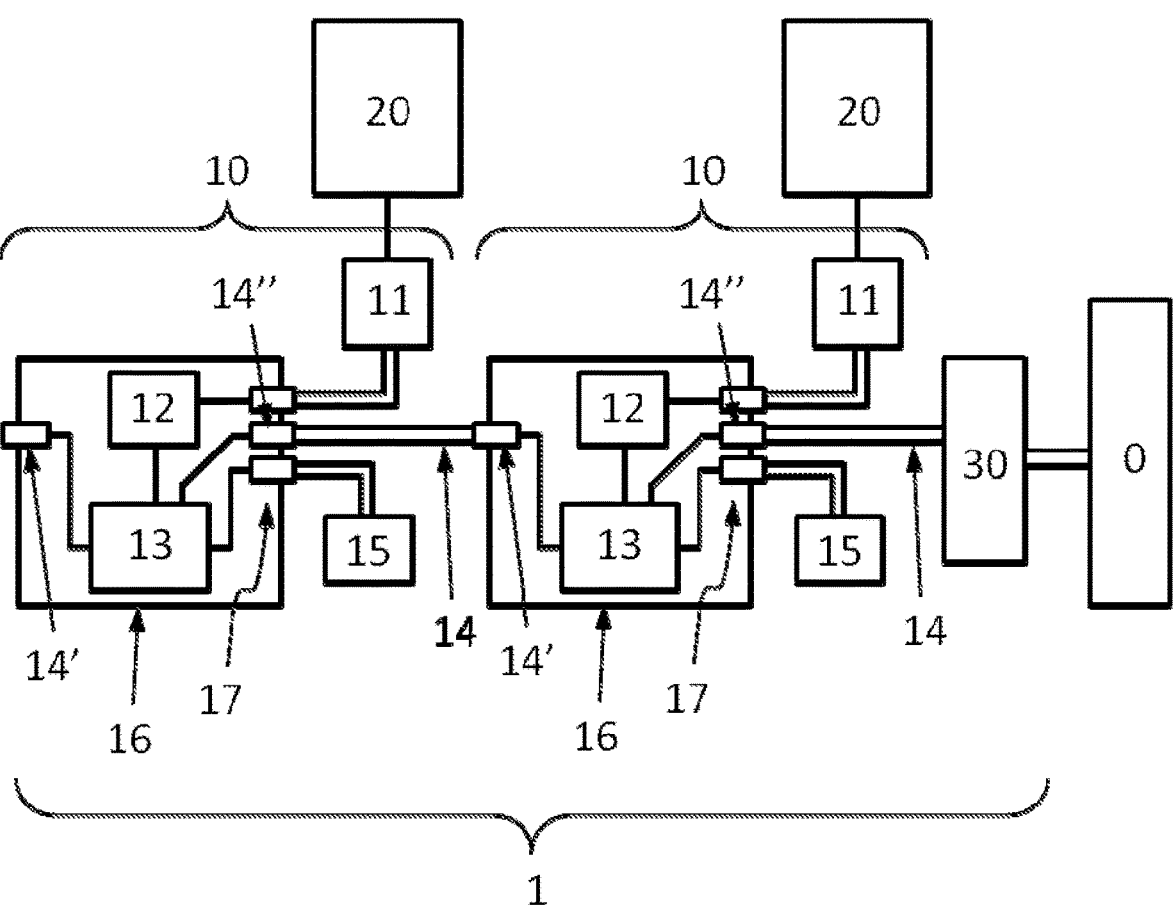
FIG. 1 is a block diagram illustrating an embodiment of the present interface system, comprising two detection modules and a hub for communicating control signals to one electronic device.

A preferred embodiment of the present interface system is illustrated schematically as a block diagram in FIG. 1. The present embodiment comprises two detection modules (10) and a hub (30) for communicating control signals to an electronic device (0). Each detection module (10) comprises:

an electrode (11) configured and arranged to be put in electrical communication with a plant (20),
a capacitive sensor (12) in electrical communication with the electrode (11),
a control unit (13) in electrical communication with the capacitive sensor (12),
a user-accessible potentiometer (15) in electrical communication with the control unit (13).

In the present embodiment, a first detection module (10) is connected via its outlet communication port (14") to the inlet communication port (14') of a second detection module (10). Said second detection module (10) is connected via its outlet communication port (14") to the hub (30), the external device (0).

The capacitive sensor (12) and the control unit (13) of each detection module (10) are located in a housing (16), whereas the electrode (11) and the potentiometer (15) are arranged outside the housing (16) at the end of a shielded wire. The housing (16) comprises openings (17) through which the shielded wires pass through the housing (16) in an hermetic way. Although in this preferred embodiment the links (14) between communication ports (14', 14") have been represented by shielded cables, the links can also consist of wireless links.

Figure 2:
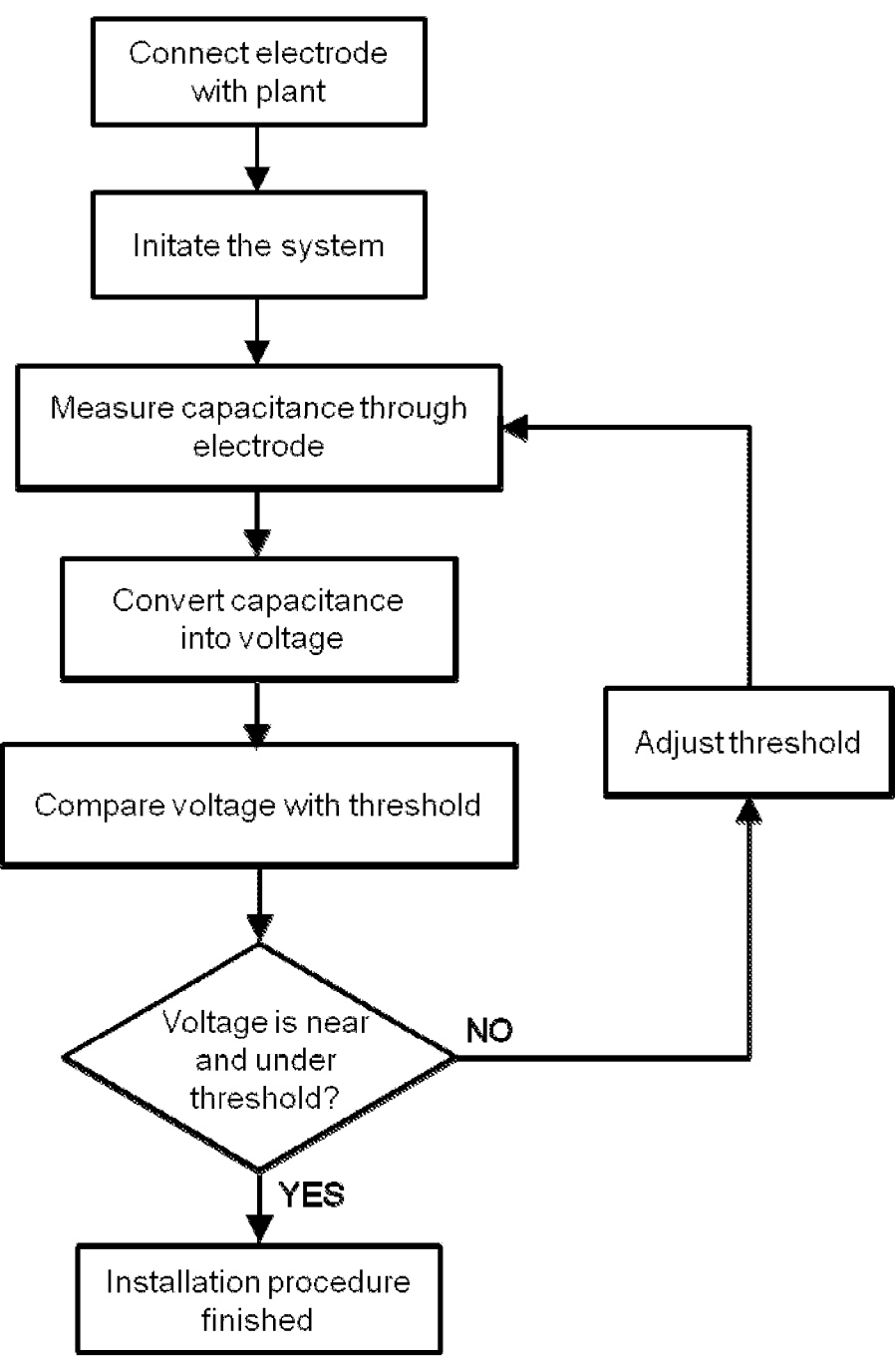
FIG. 2 is a block diagram illustrating an embodiment of an installation procedure of the present interface system.

FIG. 2 illustrates a block diagram of an embodiment of installation procedure of the present interface system. In a first step, it is necessary to electrically connect the electrodes (11) of a detection module (10) with a plant (20). Said electrical connection preferably consist on direct contact of the electrodes (11) with the substrate where the roots of the plants are buried. The substrate should have a moisture content for a better performance. As depicted from the following claims, the present interface system offers the possibility of adjusting the threshold value thanks to a user-accessible potentiometer (15). In this installation procedure, after initiating the system, the capacitive sensors (12) measure the capacitance detected through the corresponding plant (20) by means of the electrodes (11) and convert said capacitance into voltage values. The control unit (13) steadily reads said voltage values and compares them with a threshold value while adjusting the threshold value. When the user considers said voltage values being near but under the threshold value, the installation procedure can be considered completed.

Figure 3:
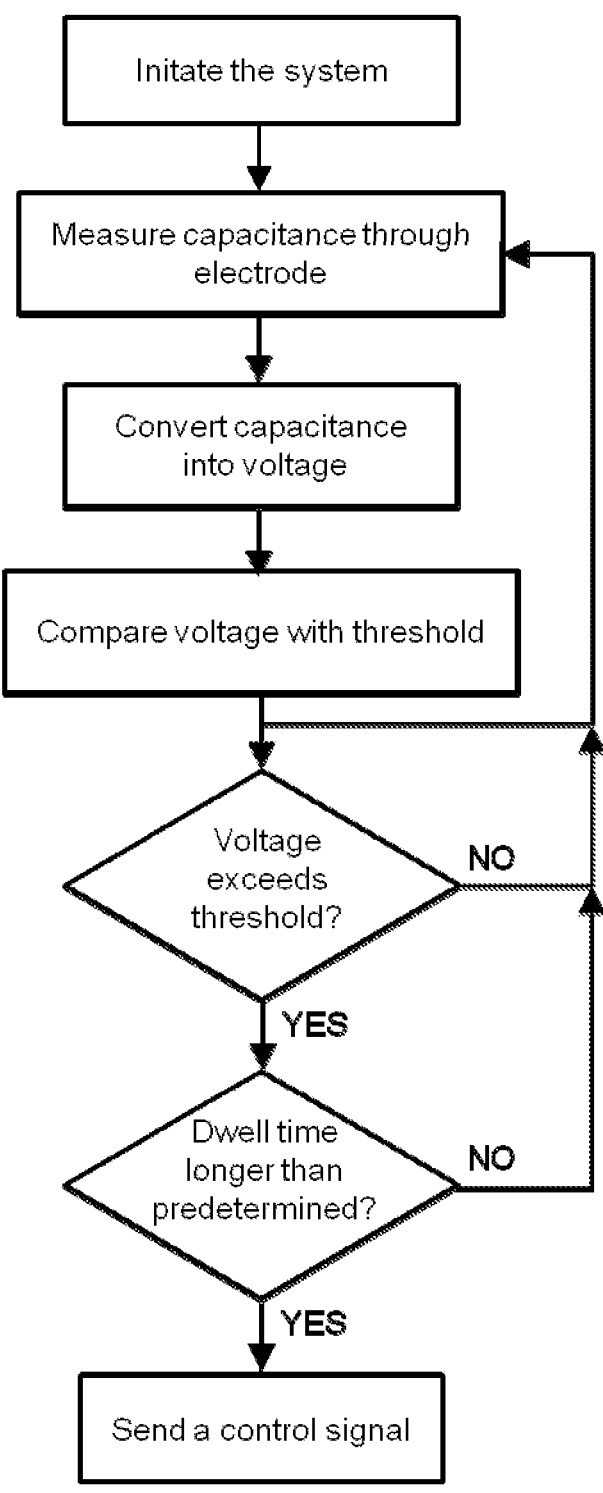
FIG. 3 is a block diagram illustrating a first embodiment of the present method for communicating control signals to one or more electronic devices.

FIG. 3 illustrates a block diagram of a first embodiment of the present method for communicating control signals to one or more electronic devices. After initiating the system, the capacitive sensors (12) measure the capacitance detected through the corresponding plant (20) by means of the electrodes (11) and convert said capacitance into voltage values. The control unit (13) steadily reads said voltage values and compares them with the threshold value. When the control unit (13) detects a voltage value exceeding the threshold value, a so-called dwell time starts being measured, which indicates the duration for which the voltage values rate above the threshold value. The control unit (13) interprets that there has been a coupling between the subject and the plant (20) only when said measured dwell time is longer than a predetermined minimum dwell duration. Only then, the control unit (13) sends the corresponding control signal to an external device (0) via said communication ports (14', 14") and hub (30). This minimum dwell duration is preferably set to 200 milliseconds. When the measured dwell time is less than said minimum dwell duration, the control unit (13) is configured to discard the supposed coupling as a false positive.

Figure 4:
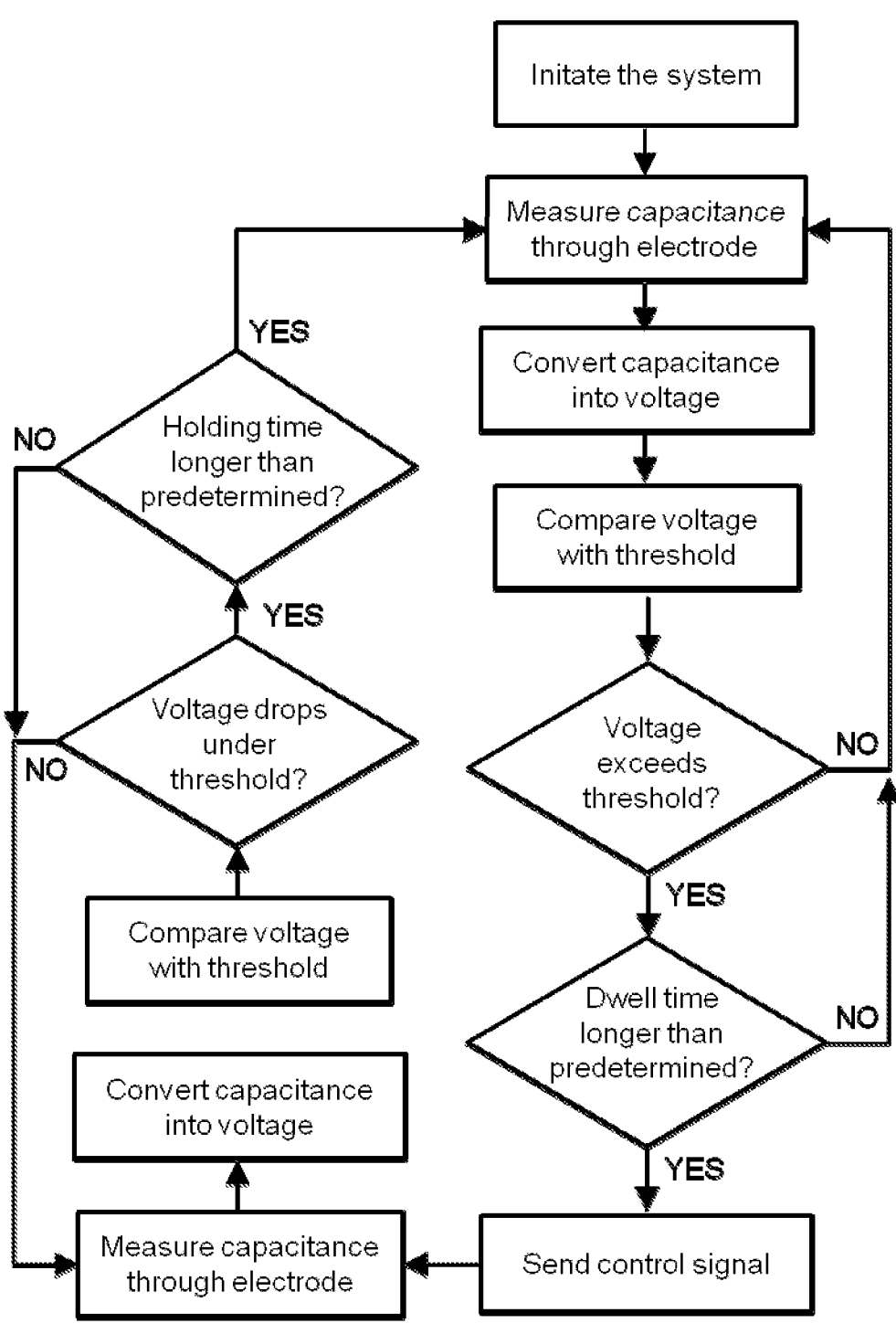
FIG. 4 is a block diagram illustrating a second embodiment of the present method for communicating control signals to one or more electronic devices.

FIG. 4 illustrates a block diagram of a second embodiment of the present method. Compared to the previous first embodiment, after interpreting that there has been a coupling between the subject and the plant (20), this second embodiment further comprises start measuring a so-called holding time when a voltage value drops under the threshold value. The holding time indicates the duration for which the voltage values rate under the threshold value. The control unit (13) interprets that said coupling has been interrupted by the subject on purpose only when said measured holding time is longer than a predetermined holding duration. Only then, the control unit (13) gets ready for interpret a new coupling. This holding duration is preferably set to 250 milliseconds. When the measured holding time is less than said minimum holding duration, the control unit (13) is configured to interpret that said coupling has not been interrupted.

Figure 5:
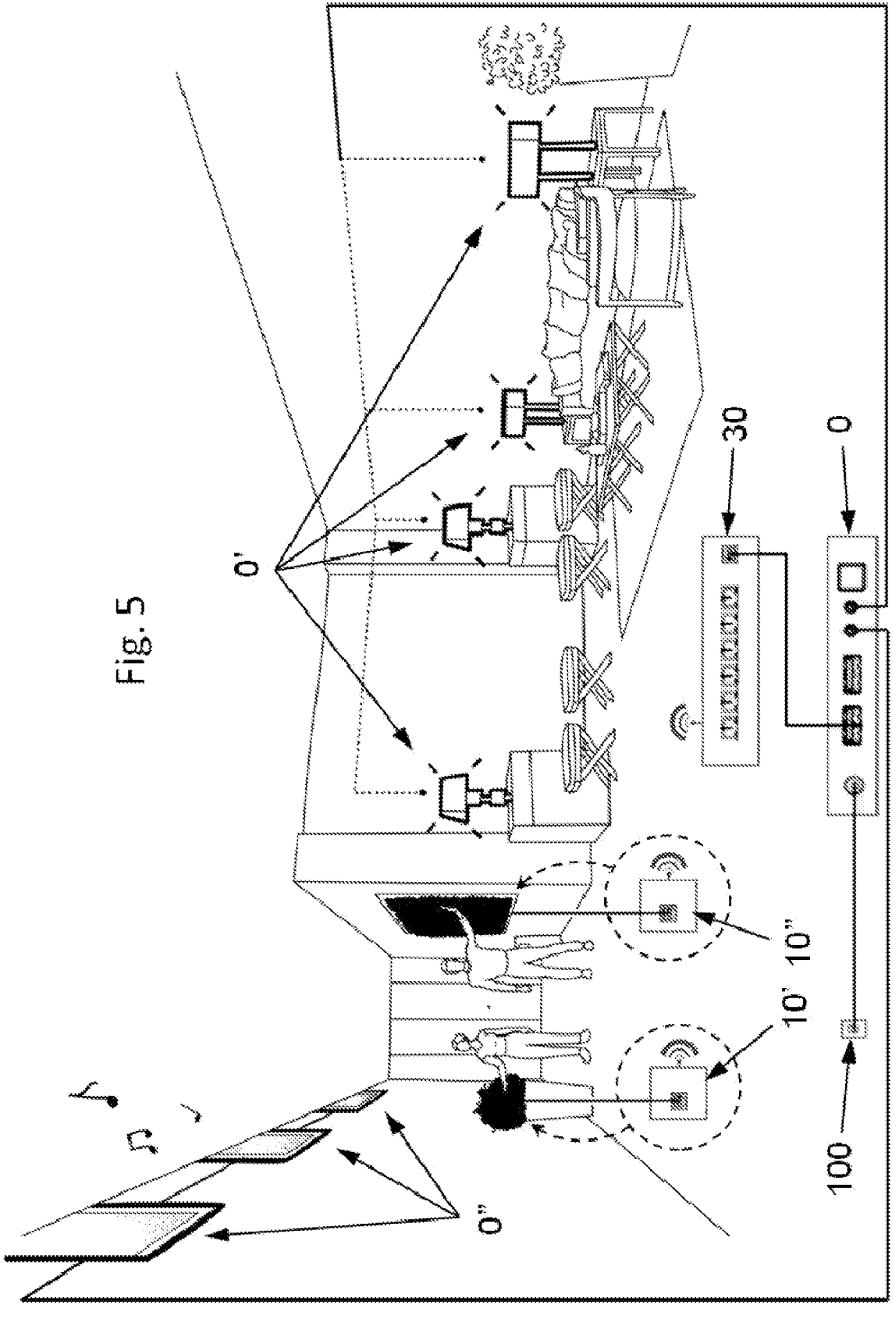
FIG. 5 is an representation of an example embodiment of the present interface system for communicating control signals to a group of lights and a group of speakers.

FIG. 5 represents an example situation where an embodiment of the present interface system is implemented. In this case, it comprises two detection modules (10', 10") linked via WIFI to a hub (30), which is configured to send control signals to a PC as external device (0). At the same time, this PC is connected to a power plug (100), a group of lights (0') and a group of speakers (0"), as well as configured to send corresponding controls signals to said lights (0') and speakers (0"). In this embodiment, an electrode (not shown) of a first detection module (10') is connected to a first plant (20'), which is responsible of the control signals received by the lights (0'). This first detection module (10') has been illustrated outside the pot of the first plant (20'), but it is located inside it, as indicated by its dotted arrow. Another electrode (neither shown) of a second detection module (10") is connected to a second plant (20"), which is responsible of the control signals received by the speakers (0"). This second detection module (10') has been also illustrated outside the second plant (20"), but it is integrated in the wall and covered by said plant (20"), as suggested by its dotted arrow.

The invention claimed is:

1. An interface system for communicating control signals to one or more electronic devices, the interface system comprising:

One or more detection modules for detecting capacitance variations in one or more plants, comprising:

one or more electrodes configured and arranged to be put in electrical communication with the plant;

one or more capacitive sensors in electrical communication with the one or more electrodes, and configured to measure capacitance through the one or more electrodes and output voltage values; and a control unit in electrical communication with one of the one more capacitive sensors, the control unit having at least one communication port connectable to one of the one or more detection modules or to one or more external devices, the control unit being configured to receive said voltage values, process the received voltage values and obtain processed voltage values, compare said processed voltage values with a threshold value, and send a control signal to the one or more external devices via said at least one communication port when said processed voltage values exceed the threshold value; and a user-accessible potentiometer in electrical communication with the control unit, the potentiometer being configured to adjust said threshold value, wherein each of said one or more detection modules is configured for electrical communication with each of the one or more plants, and wherein the one or more plants are of a crass kind.

2. The interface system according to claim 1, wherein the one or more plants comprise roots buried in a moist substrate and at least one of the one more electrodes is in direct contact with a moist substrate.

3. The interface system according to claim 1, wherein the interface system includes a hub and two or more detection modules, with more than one detection module being in communication with the hub, which is configured to receive control signals and redirect the control signals to the one or more external devices.

4. The interface system according to claim 1, wherein the control unit is further configured to apply a moving average algorithm to the received voltage values during a time interval and calculate average voltage values, wherein said processed voltage values include the average voltage values.

5. The interface system according to claim 1, wherein the control unit is further configured to measure a dwell time during which the processed voltage values are above the threshold value and, if said dwell time is shorter than a predetermined dwell duration, avoid sending the control signal.

6. The interface system according to claim 5, wherein the control unit is configured to measure, when said dwell time is longer than the predetermined dwell duration and the processed voltage values are below the threshold value, a holding time during which the processed voltage values are below the threshold value and, if said holding time is shorter than a predetermined holding duration, avoid sending a new control signal.

* * * * *